United States Patent [19]

Haruki

[11] 3,985,016
[45] Oct. 12, 1976

[54] CHROMATOGRAPH

[75] Inventor: Tatsuro Haruki, Kyoto, Japan

[73] Assignee: Shimadzu Seisakusho Ltd., Kyoto, Japan

[22] Filed: Dec. 2, 1970

[21] Appl. No.: 94,576

[30] Foreign Application Priority Data
Dec. 10, 1969 Japan.................. 44-99598

[52] U.S. Cl. .......................... 73/23.1; 73/422 GC
[51] Int. Cl.² ........................................ G01N 31/08
[58] Field of Search ............... 73/23.1, 422 GC, 23; 23/254 R, 232 E, 254 E; 55/67, 197, 386

[56] References Cited
UNITED STATES PATENTS

| | | | |
|---|---|---|---|
| 3,285,701 | 11/1966 | Robertson | 73/23.1 X |
| 3,327,520 | 6/1967 | Stapp | 73/23.1 |
| 3,566,698 | 3/1971 | Sheppard | 73/422 GC |

*Primary Examiner*—Richard C. Queisser
*Assistant Examiner*—Stephen A. Kreitman
*Attorney, Agent, or Firm*—Fidelman, Wolffe & Waldron

[57] ABSTRACT

A chromatograph provided with a new and improved purge system for the sample introducing chamber, wherein a first carrier fluid supplying conduit is connected to the chamber adjacent to the sample injection port thereof and a second carrier fluid supplying conduit is connected to the fluid path between the column and the connecting point of the first conduit and the chamber. When a sample is injected into the chamber for analysis, the carrier fluid is supplied into the chamber through the first conduit to carry the sample components into the column, and when the analysis has been completed, the carrier fluid is introduced into the fluid path through the second conduit to flow upstream through the chamber, thereby preventing any of the sample components remaining in the chamber from entering the column to cause "ghost" peaks or baseline fluctuation in the chromatogram.

5 Claims, 6 Drawing Figures

CHROMATOGRAPH

This invention relates to a chromatograph provided with a new and improved purge system for the sample introducing chamber, which is capable of effectively eliminating "ghost" peaks or baseline fluctuation in the chromatogram.

Although the following description is given in connection with a gas chromatograph, it should be noted that it is only by way of example and the invention is also applicable to various other types of chromatographs.

In measurement of a liquid sample by a prior art gas chromatograph, the "ghost" peaks or baseline fluctuation in the chromatogram pose a serious and difficult problem. When the analysis of a sample has been finished, some of the sample components tends to remain attached to the inner surface of the sample introducing chamber. This is especially true with samples having high boiling points, which have not been completely vaporized during the analysis but remain in the sample introducing chamber. In the next run of analysis, even when a sample is yet to be introduced, those remaining substances or the impurities decomposed from the tubber cap which seals the sample injection port of the chamber are carried into the column little by little, thereby causing fluctuation of the baseline in the chromatogram.

In a programmed temperature operation of the chromatograph, the baseline fluctuation is so great that peaks sometimes appear where there should actually be no peaks. The cause for this is as follows: When a run of analysis has been finished in the chromatograph, the column temperature is lowered. As previously mentioned, however, the remaining portion of the sample introduced for the previous analysis, or the impurities decomposed from the rubber cap of the sample introducing chamber have been carried as far as the inlet of the column and stay there since the temperature of the column has now been lowered. Therefore, when the column temperature is raised again for the next analysis, the substances remaining near the inlet of the column begin to travel through the column. The situation is as if a sample had been injected into the chamber though actually there were no sample introduced, with resulting appearance of false or "ghost" peaks in the chromatogram obtained.

Accordingly, it is one object of the invention to provide a chromatograph having a new and improved purge system for the sample introducing chamber, which is capable of eliminating "ghost" peaks in the chromatogram.

Another object of the invention is to provide a chromatograph having a new and improved purge system for the sample introducing chamber, which is capable of eliminating the baseline fluctuation in the chromatogram.

The chromatograph of the invention is characterized by the provision of a pair of carrier fluid supplying conduits, a first connected to the sample introducing chamber adjacent to the upstream end thereof and the second connected to the fluid path between the column and the connecting point of the first conduit and the chamber. In one preferred embodiment of the invention, carrier fluid is alternatively supplied into the sample introducing chamber through a selected one of the two conduits. That is, when a sample has been injected into the chamber, the carrier fluid is introduced into the chamber through the first conduit, that is, the conduit which is connected to the upstream end of the chamber, with the other conduit being blocked, so that the carrier fluid carries the sample into the column in the well known manner. When the analysis has been completed, however, the carrier fluid is introduced through the second conduit, with the first conduit being shut off from the fluid source but open to the atmosphere, so that the carrier fluid flows through the sample introducing chamber from its downstream to upstream ends, thereby preventing any of the remaining sample components and/or the impurities decomposed from the rubber cap of the injection port from entering the column to cause errors in the measurement.

The invention will be more clearly understood by reading the following description of some preferred embodiments thereof with reference to the accompanying drawings, wherein the same reference symbols in different figures denote corresponding parts, and wherein.

Figure 1:
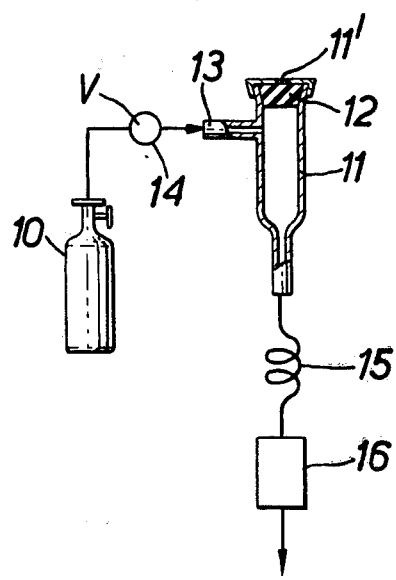
FIG. 1 is a schematic diagram of a typical gas chromatograph.
Figure 2:
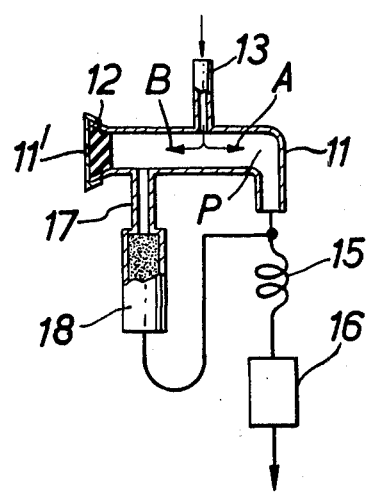
FIG. 2 is a schematic diagram of a prior art chromatograph provided with a device for reducing base line fluctuation or "ghost" peaks in the chromatogram.

Referring first to FIG. 1, there is shown a typical layout of a gas chromatograph comprising a source of carrier gas 10; a sample introducing chamber 11 having a sample injection port 11' at one end thereof with a rubber cap 12 closing the port; a conduit 13 connecting the source 10 to the upstream end of the chamber 11, with a control valve 14 inserted in the conduit 13; a column 15 connected to the downstream side of the sample introducing chamber 11; and a detector 16 connected to the downstream side of the column. As previously mentioned, a fraction of the sample introduced for the previous analysis and/or the impurities decomposed from the material of the cap of the sample injection port are likely to be carried into the column in the next analysis so as to cause occurrence of ghost peaks or fluctuation of the baseline in the chromatogram obtained. To prevent such an undesirable result, an arrangement schematically shown in FIG. 2 has been proposed, in which the carrier gas supplying conduit 13 is connected to the sample introducing chamber 11 about the middle of the length thereof, with an outlet 17 formed in the chamber adjacent to the sample injection port 11' thereof. The outlet 17 is connected to the inlet end of the column through a pipe 18 filled with activated charcoal. With this arrangement, the carrier gas introduced through the conduit 13 is divided into two stream A and B. The stream A flows into the column 15 while the stream B flows in the opposite direction toward the sample injection port 11' and carries the substances, if any, decomposed from the material of the cap 12 into the outlet 17 and thence into the pipe 18, where the charcoal adsorbs the impurities, thereby preventing them from entering the column 15. This arrangement, however, has the following defect: A sample is injected into the chamber 11 by means of a syringe or the like, the outer end of the needle of which is inserted as far as a point P beyond the carrier gas inlet 13 where the gas is split into the two streams. When the sample injected is rapidly vaporized and expanded due to the high temperature in the chamber so that some of the vapor even flows upstream beyond the splitting point of the carrier gas so as to be carried by the stream B into the outlet 17. This loss of a portion of the sample to be analyzed certainly results in an error in the quantitative measurement.

Figure 3:
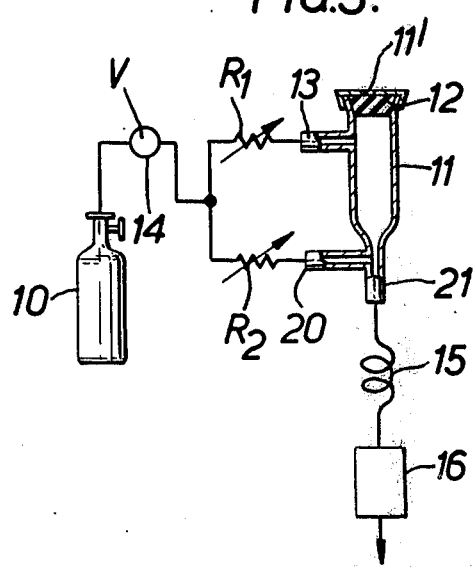
FIGS. 3 to 6 are schematic diagrams of different embodiments of the invention.

The defect has been eliminated by the arrangements of the invention as shown in FIGS. 3 to 6. Referring first to FIG. 3, there is shown a first carrier gas supply conduit 13 connected to the sample introducing chamber 11 adjacent to the upstream end thereof and, in addition to this first supply conduit, a second carrier gas supply conduit 20 connected to a fluid path 21 between the connecting point of the conduit 13 and the chamber 11 and the inlet of the column 15. The two conduits 13 and 20 have their other ends connected to the source of carrier gas 10 through flow resistors or regulators R1 and R2, respectively. Suppose that the resistors R1 and R2 are set to the same resistance value. The carrier gas from the source 10 is divided half and half into the two conduits 13 and 20. Since it is the gas introduced through the first conduit 13 alone that carries the sample components into the column 15, it takes twice as long a time for the sample components to be completely carried into the column 15 as with the prior art arrangement. However, when there is no sample introduced into the chamber 11, the carrier gas supplied through the second conduit 20 helps reduce the concentration of the remaining sample components or impurites carried by the gas from the first conduit 13 into the column to half the value which would otherwise result from the prior art arrangement, thereby reducing the ghost peaks or fluctuation of the baseline in the chromatogram.

Figure 4:
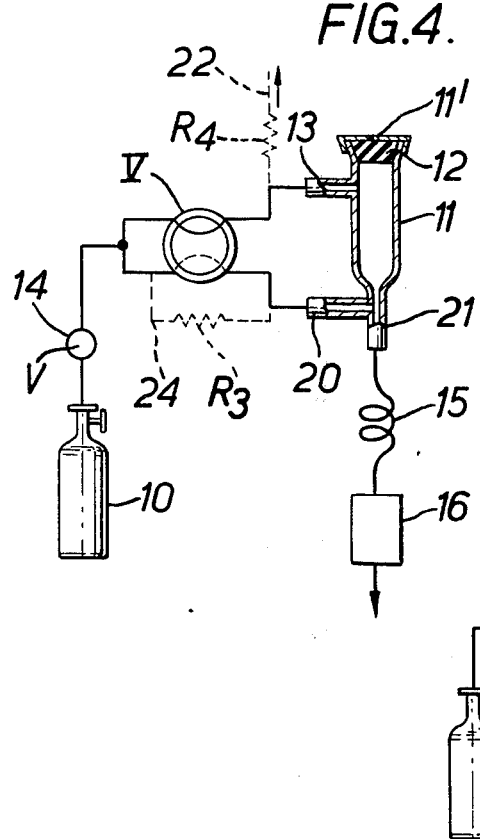
Figure 5:
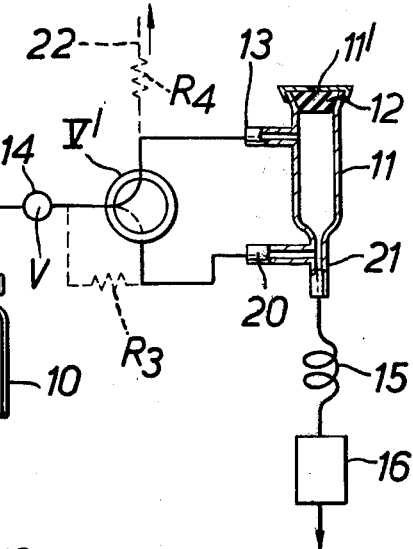
Figure 6:
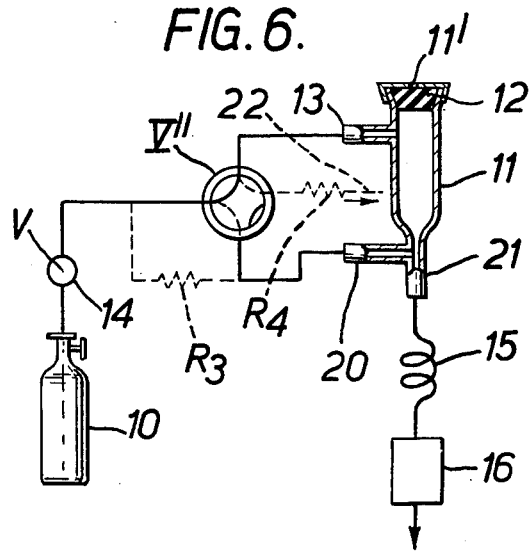

The arrangements of FIGS. 4 to 6 are more effective than that of FIG. 3. In FIG. 4, a flow path change valve V is inserted in the carrier gas supply conduits 13 and 20 in such a manner as to alternatively connect one of the conduits to the carrier gas source 10 while blocking the other. When a sample has been injected into the chamber 11, the valve V is positioned as indicated by the real line in FIG. 4, so that the carrier gas from the source 10 is introduced into the chamber 11 through the upstream conduit 13 alone. Therefore, the time required for all the sample injected into the chamber 11 to be carried into the column 15 does not become any longer than with the arrangement of FIG. 1. When the analysis of the sample has been completed, the valve V is switched to the position shown by the dotted line, whereupon the carrier gas from the source 10 is supplied through the other conduit 20 alone. Under the condition, there is no carrier gas supplied by the conduit 13 to flow in the chamber 11 toward the column 15, so that any remaining sample components or impurities in the chamber 11 are prevented from entering the column to cause ghost peaks or baseline fluctuation in the chromatogram.

If the carrier gas supply conduit 13 is opened to the atmosphere as at 22 through a flow resistor R4, part of the gas supplied through the conduit 20 flows upstream through the chamber 11 into the conduit 13 and thence exhausted into the open air through the resistor R4, thereby all the more effectively preventing the unnecessary substances from entering the column 15.

A by-pass 24 shown by the dotted line in FIG. 4 with a flow resistor R3 may be connected across the valve V to supply a small amount of the gas into the path 21 through the conduit 20 when the valve V is positioned so as to render the conduit 13 conductive, thereby preventing the carrier gas containing the sample components from being deflected into the conduit 20 in the reverse direction. The by-pass has a smaller flow capacity than the conduit 13.

The arrangement of FIG. 5 differs from that of FIG. 4 only in that a valve V' of a different structure is employed to selectively connect the source 10 to either of the conduits 13 and 20. For analysis of a sample injected into the chamber 11, the valve V' is positioned as indicated by the real line, while when the analysis has been completed, the valve is switched over to the position shown by the dotted line. The operation of the system of FIG. 5 is substantially the same as in FIG. 4 so that no explanation thereof will be required.

In the arrangements of FIGS. 4 and 5, pressure fluctuation in the chamber 11 may cause the sample injected therein to leak out through the resistor R4. The arrangement of FIG. 6 is directed toward preventing such loss of the sample and resulting error in the measurement. Here, the exhaust pipe 22 with the flow resistor R4 is so associated with a valve V'' that for analysis of the sample injected into the chamber 11, the valve connects the conduit 13 to the gas source 10, interrupting the communication between the conduit 13 and the exhaust pipe 22, while at other times the valve is so positioned as to connect the other supply conduit 20 to the source, establishing the communication between the exhaust pipe 22 and the conduit 13 and consequently the chamber 11. The operation of this system is also substantially the same as the previous embodiments.

I claim:
1. A chromatograph comprising:
    a sample introducing chamber having a sample inlet port at its upstream side;
    a column having one end connected to the downstream side of said chamber;
    a first conduit connected at one end to said chamber adjacent to said inlet port at a first port;
    a second conduit connected at one end to said chamber between said column and said first port at a second port;
    said first and second ports being continuously in communication with said column;
    means for providing carrier fluid;
    valve means connected between said fluid providing means and said first and second conduits for directing carrier fluid from said fluid providing means to said chamber and said column simultaneously through a selected one of said first or second conduits; and
    means connected to said first conduit for regulating an opening of said first conduit to the atmosphere whereby said carrier fluid introduced into said chamber by said first conduit carries a sample into said column and part of said fluid introduced into said chamber by said second conduit purges said chamber through said atmosphere regulating means while the remaining part of said fluid continues to carrier said sample through said column.

2. The chromatograph of claim 1 wherein said atmosphere regulating means includes a flow resistor and means for connecting said first conduit to said atmosphere through said flow resistor when said valve means shuts off said first conduit from said fluid providing means.

3. The chromatograph of claim 1, further including a by-pass connected to said second conduit across said valve means, said by-pass having a smaller flow capacity than said first conduit.

4. The chromatograph of claim 2, further including a by-pass connected to said second conduit across said valve means, said by-pass having a smaller flow capacity than said first conduit.

5. The chromatograph of claim 1 further including a detector connected to the downstream side of said column.

* * * * *

UNITED STATES PATENT OFFICE
CERTIFICATE OF CORRECTION

PATENT NO. : 3,985,016
DATED : October 12, 1976
INVENTOR(S) : TATSURO HARUKI

It is certified that error appears in the above-identified patent and that said Letters Patent are hereby corrected as shown below:

Column 1, line 25, change "tubber" to --rubber--.

Claim 1, line 17, cancel "simultaneously".

Claim 1, line 28, change "carrier" to --carry--.

Signed and Sealed this

First Day of March 1977

[SEAL]

Attest:

RUTH C. MASON
*Attesting Officer*

C. MARSHALL DANN
*Commissioner of Patents and Trademarks*